United States Patent
Djeu

[11] Patent Number: 5,968,038
[45] Date of Patent: Oct. 19, 1999

[54] LASER POWERED HEATING ELEMENTS

[75] Inventor: Nicholas I. Djeu, Tampa, Fla.

[73] Assignee: University of South Florida, Tampa, Fla.

[21] Appl. No.: 08/741,540

[22] Filed: Oct. 31, 1996

[51] Int. Cl.⁶ .................................................. A61B 17/36
[52] U.S. Cl. .................................. 606/16; 606/17; 606/2; 606/13
[58] Field of Search .................................. 606/14, 15, 16, 606/17, 10, 11, 12, 13, 9, 4, 5, 6; 607/88, 89

[56] References Cited

U.S. PATENT DOCUMENTS

| | | | |
|---|---|---|---|
| 4,660,925 | 4/1987 | McCaughan, Jr. | 606/16 |
| 4,693,556 | 9/1987 | McCaughan, Jr. | 606/16 |
| 4,729,373 | 3/1988 | Peyman | 606/16 |
| 5,078,711 | 1/1992 | Kakami et al. | 606/16 |
| 5,196,005 | 3/1993 | Doiron et al. | 606/7 |
| 5,209,748 | 5/1993 | Daikuzono | 606/16 |
| 5,242,437 | 9/1993 | Everett et al. | |
| 5,275,596 | 1/1994 | Long et al. | |
| 5,304,228 | 4/1994 | Prince | |
| 5,320,620 | 6/1994 | Long et al. | |
| 5,342,355 | 8/1994 | Long | |
| 5,370,649 | 12/1994 | Gardetto et al. | |
| 5,380,317 | 1/1995 | Everett et al. | |
| 5,520,681 | 5/1996 | Fullet et al. | 606/17 |
| 5,527,308 | 6/1996 | Anderson et al. | 606/14 |
| 5,549,600 | 8/1996 | Cho | 606/15 |
| 5,562,657 | 10/1996 | Griffin | 606/17 |
| 5,782,771 | 7/1998 | Hussman | 606/2 X |

OTHER PUBLICATIONS

Hoen, et al., "Thermomocehanical Data Storage Using a Fiber Optic Stylus", American Institute of Physics, Appl. Phys. Lett. vol. 64, No. 3, pp. 267–269, Jan. 17, 1994.

Phomsakha, et al., "Fiber–Optic High–Tempertute Thermal Source", American Institute of Physics, Rev. Scl. Instrum. vol. 67, No. 8, pp. 2987–2988, Aug. 1996.

*Primary Examiner*—Linda C. M. Dvorak
*Assistant Examiner*—Sonya Harris-Ogugua
*Attorney, Agent, or Firm*—Calfee, Halter & Griswold, LLP

[57] ABSTRACT

A laser-powered fiberoptic heating element comprises a crystalline optic fiber fusion bonded to a crystalline heat-generating tip section.

33 Claims, 1 Drawing Sheet

LASER POWERED HEATING ELEMENTS

The present invention relates to novel laser-powered heating elements.

Laser-powered fiberoptic heating elements are known. For example, U.S. Pat. No. 5,164,945, U.S. Pat. No. 5,342,355 and U.S. Pat. No. 5,370,649 disclose surgical devices comprising laser-transmitting optic fibers having heat generating tip elements located on the distal ends of the fibers.

In such heating elements, the heat generating tips may take the form of a shaped piece of a ceramic capable of absorbing laser light, such as titanium carbide or tungsten carbide. In such cases, the pre-formed tip is usually attached to the optic fiber by adhesives such as epoxies or mechanical connectors such as end caps or the like. In other heating elements, the tip is formed from a material substantially transparent to laser light, the tip being provided with a coating of a laser light-absorbing material such as titanium, chromium, nickel, zirconium, molybdenum, tantalum, tungsten or titanium nitride.

Each of these designs has inherent drawbacks. For example, those designs using adhesives or plastic materials to attach the heating element to the optic fiber are limited in terms of maximum useful temperature, since the plastic or adhesive will melt or decompose if heated too high. Designs which use connectors formed from metal risk excessive and unwanted heating of the connector. Loss of integrity due to the metal's higher coefficient of thermal expansion is also a concern. In designs which rely on coatings for heat generation, coating thickness and hence overall performance are often limited because of the esoteric coating procedures typically used to apply the laser-absorbing material. The integrity of such coatings can also be a problem due to mismatch of coating and substrate coefficients of thermal expansion.

As a result of these problems, currently-available heating elements are inherently limited both in terms of physical reliability or ruggedness as well as the maximum operating temperatures they can tolerate before breakdown.

Accordingly, there is a need for laser-powered fiberoptic heating elements which avoid surface coatings of laser-absorbing materials and which also avoid plastic or metal connectors, so that the drawbacks inherent in such materials can also be avoided.

SUMMARY OF THE INVENTION

In accordance with the present invention, a novel laser-powered fiberoptic heating element is provided, the heating element comprising a crystalline optic fiber having a crystalline heat-generating tip element fused thereto.

Because the optic fiber and the tip element are crystals which are fused together, mechanical or adhesive bonding systems can be totally eliminated. Also, because the tip element is capable itself of converting laser light into heat energy, special coatings of laser-absorbing materials are also avoided. As a result, the inventive heating element can achieve superior performance characteristics compared with earlier designs.

For example, the inventive heating element can achieve higher operating temperatures than associated with conventional designs, since the only constraint on its maximum operating temperature is the melting temperatures of its optic fiber and tip element. In addition, the inventive heating element is more rugged than earlier designs since degradation of adhesives and/or plastic connectors over time, especially at higher temperatures, is avoided.

DETAILED DESCRIPTION

Figures 1, 2:
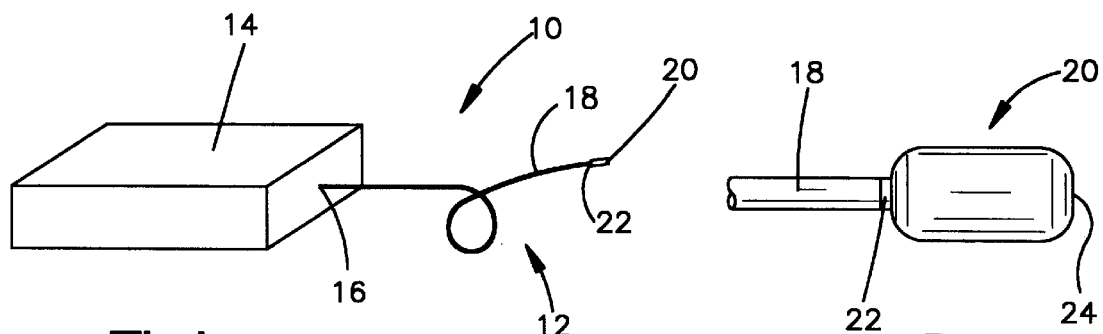
FIG. 1 is a schematic view of a heating assembly produced in accordance with the present invention including the laser-powered fiberoptic heating element of the present invention and a laser connected thereto.
FIG. 2 is a partial exploded view showing the heat-generating tip of the heating element of FIG. 1.

As shown in FIGS. 1 and 2, a heating assembly generally indicated at 10 is composed of the inventive laser-powered fiberoptic heating element 12 and a laser 14 attached thereto. The output from laser 14 is coupled into the input end 16 of the fiberoptic heating element 12 of the present invention. The latter is comprised of a length of a crystalline fiber 18 which is highly transmitting of the particular laser light generated in laser 14 and a heat-generating tip section 20 which absorbs strongly at that laser wavelength. Optic fiber 18 is fused to heat-generating generating tip section 20 at junction 22 by any of the known means of fusing two crystalline objects together.

The optic fiber and the heat-generating tip sections of the inventive heating element can be made from a wide variety of different crystalline materials. For each device made in accordance with the present invention, the optic fiber should transmit over its entire length a substantial portion of the laser light generated by the laser source (preferably at least 50%, more preferably at least 90%). Similarly, the heat-generation tip section should absorb a substantial portion (preferably at least 50%, more preferably at least 90%) of the laser light received from the optic fiber and convert it to heat energy. In addition, the optic fiber and the tip section should preferably be crystallographically compatible as well.

By "crystallographically compatible" is meant that the crystals forming the optic fiber and the tip section are similar enough in structure to promote bonding of the two crystals together at their interface. In this regard, it is well known that when two crystals are fused together, the similarity in the pattern of atoms in each crystal at their interface plays an important part in the strength of the fusion bond so formed. For example, crystal pairs which match one another in terms of the number, arrangement and spacing of atoms in their bonding planes typically form strong bonds as the "common" crystal structure of the two is "continued" from one to the other. Similarly, crystal pairs whose crystal structures "register" with one another at the interface, i.e. which have the same arrangement of atoms but whose atomic spaces are in multiples or rational fractions of one another, are also known to form strong bonds with one another. However, crystal pairs which have little or no similarity in the number, arrangement and spacing of the atoms at their fusion interface typically have no significant bond strength, since the structure of the two crystals is not continued from one to the other.

In accordance with the present invention, the crystals of the optic fiber and the tip section in each heating element preferably should match or at least register with one another. In any event, these crystal structures should at least be similar enough so that the fusion bond between the two remains intact when the heat element is subjected to normal handling and manipulation, over repeated use cycles, in its intended manner of use.

In addition to being crystallographically compatible, the different crystalline materials used to form the optic fiber and the heat-generating tip section should also be thermomechanically similar. By "thermomechanically similar" is meant that the two crystals should have coefficients of thermal expansion which are close enough so that the integrity of the fusion region is not compromised as a result of differential thermal expansion upon repeated reuse of the device.

In order to determine if a particular pair of candidate crystals are crystallographically and thermomechanically compatible, a test heating element can be formed from these crystals and subjected to a test protocol of mechanical handling and repeated thermal cycling. If the test device so made does not degrade under conditions in the protocol approximating those to be encountered in use, then the combination of crystals has the desired crystallographic and thermomechanical compatibility for the particular utility intended.

A wide variety of crystalline materials which can transmit substantial portions of laser light at particular wavelengths, and hence are useful in making the optic fibers of the inventive laser-powered heating element, are known. For example, many crystalline oxide materials are useful for this purpose. Specific examples are YAG ($Y_3Al_5O_{12}$), $Al_2O_3$, $Y_2O_3$ and $ZrO_2$—$Y_2O_3$.

A wide variety of crystalline materials which can convert substantial portions of laser light received into heat energy, and hence are useful in making the heatgenerating tip section of the inventive laser-powered heating element, are also known. Specific examples are Nd-doped YAG, Tm/Dy co-doped $Y_2O_3$ and $Cr_2O_3$.

The optic fiber and heat-generating tip section of the inventive laser-powered fiberoptic heating element can be joined by any technique in which two crystals are fused together. For example, the heat-generating tip section, arranged in the proper orientation with respect to the optic fiber, can be fused to the optic fiber by the application of heat from a laser. Specifically, the laser heated pedestal growth techniques illustrated in U.S. Pat. No. 4,040,890, U.S. Pat. No. 4,421,721 and U.S. application Ser. No. 08/327,454 filed Oct. 21, 1994, the disclosures of which are incorporated herein by reference, can be used to grow the tip section on the optic fiber and, if desired, to grow the optic fiber itself before the tip element is grown thereon.

In operation of the inventive heating element, laser light absorbed by the heat-generating tip section is converted into thermal energy through electron-phonon interaction within the crystal. Two generic types of processes are possible for this conversion. The first type takes place in doped crystals. The dopant ions are raised to electronically excited states as a result of absorption of photons. The excited ions can generally relax back to their ground state by either radiative or nonradiative processes. The latter are mediated by electron-phonon interactions, and depend strongly on the energy level structure of the ion. Sometimes they can also depend on the concentration of the dopant ions. For efficient conversion of optic energy to thermal energy, the nonradiative processes should dominate over the radiative ones. Sometimes this can be facilitated by doping the crystal with more than one species of ions.

The second type of conversion takes place in "pure" crystals. Here electrons excited to the conduction band can again relax by radiative or nonradiative means. If the latter occurs to a significant degree, efficient conversion of optic energy to thermal energy can also be obtained.

The surface temperature profile of tip section 20, that is, the temperature of tip section 20 as a function of distance from fusion junction 22, generally depends on a number of factors. In a tip section of uniform composition and cross-section, and not having a temperature-dependent absorption coefficient, the rate of heat generation for a location remote from junction 22 is less than that for a location closer to junction 22. This is because power is attenuated as the laser radiation propagates down the length of the tip element. On the other hand, the rate of energy loss is largest at fusion junction 22 because of the large temperature gradient there as a result of conduction loss to the fiber. Therefore, in general terms, maximum surface temperature occurs somewhere between junction 22 and the very tip 24 of tip section 20. The exact location depends on the thermal conductivity, absorption coefficient, emissivity, and efficiency in photon-to-phonon conversion of the material which forms the tip section 22 as well as its physical dimensions and the atmosphere which surrounds it.

In what follows, whenever the term "temperature" of the heat-generating tip section is used, it will be understood to mean its average temperature.

The laser which powers the inventive heating element can be operated in either the continuous mode or the pulsed mode. If the laser is operated in the continuous mode, the heat-generating tip section will reach a steady-state temperature a short time after the laser is actuated. If the inventive heating element is powered by a pulsed laser, the temperature of the heat-generating tip section will rise to a maximum value and then fall back. The elapsed time for these temperature changes depends on the rates of the various radiative and non-radiative processes occurring within the heat-generating tip section. In addition, the temporal shape of the laser pulse may also affect the rise and fall times of the temperature in the pulsed mode. When a diode laser is used to energize the inventive heating element, a very compact overall system is obtained.

The optic fiber of the inventive heating element plays a dual role. It not only delivers laser light from the laser to the tip section, but it also serves as a handle by which the heat-generating tip section can be manipulated. Because of the thinness of the fiber, its temperature rapidly approaches ambient as the distance from fusion junction increases. Therefore, it is possible to provide the fiber with a protective jacket made from a heatdecomposable material such as Teflon or other plastic up to a short distance from the point of fusion. The user can then hold the fiber near the end of the jacketed portion and move the heat-generating tip element about at will.

In order to minimize heat loss by thermal conduction through the fiber, the fiber should be made as thin as possible. On the other hand, the fiber should be made sufficiently thick to provide the desired rigidity in handling. Thus, a compromise may be necessary in determining the optimal diameter for the crystalline fiber.

It should also be appreciated that another (or secondary) optic fiber can be interposed between the crystalline optic fiber and the laser, if desired. The secondary optic fiber need not be crystalline, since it will not be fusion bonded to the heat-generating tip section. Accordingly, any laser light transmitting fiber can be used for forming the secondary optic fiber.

Depending on the application, different temperature profiles along the heat-generating tip element may be desired.

This can to some extent be accommodated by using heat-generating tip sections formed from doped crystals in which the dopant concentration varies along the longitudinal direction of the tip element. For example, if maximum temperature is desired at the end of the tip section, the tip section can be made with a substantially higher dopant concentration near its end. This would increase the rate of heat generation at the end and hence the temperature there.

Figure 3:
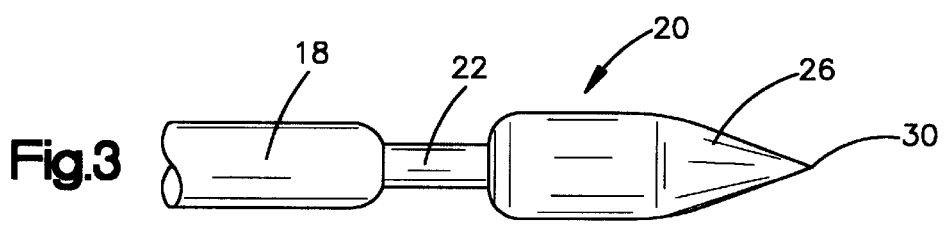
FIG. 3 is a schematic view of another laser-powered heating element of the present invention in which the heat-generating tip is indirectly attached to the optic fiber.

Alternately, the tip may terminate in a taper, as illustrated in FIG. 3. If the longitudinal rate of reduction in the cross sectional area of the tapered part exceeds the longitudinal rate of laser power attenuation, the rate of laser energy deposition per unit volume would increase towards the terminus of the heat-generating tip element, thus leading to a higher temperature there. The tip element in FIG. 3 is also shown with a metallic coating. The metal film serves to minimize leakage of laser light from the element, which could otherwise be substantial and may be undesirable for certain applications.

FIG. 3 illustrates another principle which may be used to advantage in some situations. In the heating element of this embodiment, heat-generating tip section 20 is not fused directly to optic fiber 18, but indirectly via a short length of a buffer crystal 32. This may be necessary when the desired crystal for the heat-generating tip section is not crystallographically and thermomechanically compatible with the optic fiber. Thus, buffer crystal 32 allows a wider selection of crystal combinations to be used in fiber 18 and tip section 20 than possible without the buffer crystal.

The requirements for buffer crystal 32 are that it be crystallographically compatible with both heat-generating tip section 20 and optic fiber 18 and thermomechanically compatible with tip section 20 as well. In addition, it should have enough transparency to the laser light being employed to allow the tip section 20 to reach its desired operating temperature. In this regard, it should be appreciated that a much lower transparency can be tolerated in buffer crystal 32 than in optic fiber 18, since the length of buffer crystal 32 can be made very short (~1 mm or less).

Also since the buffer crystal can be very short, it can also be made thinner than both the fiber and the heat-generating tip element, as illustrated in FIG. 3, and still afford a high degree of rigidity. Necking down the buffer region has the effect of minimizing heat loss from the heat-generating tip element through conduction to the fiber. Thus, the fiber in this case can have a significantly lower melting temperature than the heat-generating tip element. It is clear that the same construction can be used even in the absence of a buffer region. That is, a short length of the fiber near the end can be tapered to a smaller diameter before it is fused to the heat-generating tip element.

The laser-powered fiberoptic heating element of the present invention is suitable for use in a wide variety of different applications such as cutting, puncturing, surface modification, and vapor deposition. For example, it can be used for welding of micro-structures, cutting and attaching fine wires, initiating pyrolysis or other chemical reactions, and creating microscopic surface features in substrates through melting by contact. By placing it in close proximity to a substrate, highly localized thin film structures can be produced using chemical vapor deposition techniques. By utilizing gas pressures for which the mean free path is of the same scale as the distance between the surface of the object to be heated and the heating element's tip, which in turn is of the same scale as the radius of the tip itself, deposited features which are comparable in size to that of the tip should be possible. Additionally, the inventive heating element can also serve as a blackbody radiation source when operated at sufficiently high temperatures. It may also be used as a light source or simply a radiative heat source. Diverse as they are, the above applications are merely illustrative in nature, and should in no way be taken as being exhaustive in their scope.

WORKING EXAMPLE

A fiberoptic heating element made in accordance with the present invention was fabricated and tested. For the crystalline fiber and the heat-generating tip element undoped YAG and Nd-doped YAG, respectively, were employed.

An undoped YAG fiber and an Nd:YAG mini-rod were separately grown using a seed oriented along the (111) direction on a Laser Heated Pedestal Growth (LHPG) system as shown in Chang et al. *Proc. SPIE* 1104, 244 (1989). The starting feed for the optic fiber was a 1 mm×1 mm single crystal of YAG. A 20 cm long fiber with a diameter of 150 $\mu$m was obtained after two diameter reduction steps. The ends of the fiber were then polished, and transmission measurements were made at 515.4 nm. The net transmission was found to be 50%. Since the Fresnel losses at the two ends should amount to only 16%, the low transmission indicated the presence of significant defect centers in the fiber. It was therefore annealed at 1200° C. for 24 hours. The annealed fiber gave a transmission of 75%. The remaining propagation loss is attributed to a combination of residual defect centers and scattering at the imperfect wall of the fiber.

To grow the Nd:YAG mini-rod, a cold-pressed disk of 1 mm thickness consisting of $Y_2O_3$, $Al_2O_3$ and $Nd_2O_3$, in proportions so as to give 15 at. % Nd, was first prepared. It was then sintered, and a 1 mm wide strip was cut therefrom. Starting from this 1 mm×1 mm feed, again two growth steps were used to produce a mini-rod with 350 $\mu$m diameter. A 4 mm long piece of this mini-rod was cut and polished at the two ends. Absorption measurements at 514.5 nm showed that it had a net transmission of 27%. Comparison with the absorption found for a 1% Nd:YAG laser rod led to the conclusion that the mini-rod had only 5 at. % Nd instead of the intended 15%. This difference is attributed to the low distribution coefficient for Nd in YAG. See R. A. Laudise, *The Growth of Single Crystals*, Prentice-Hall, Englewood Cliffs, 1970. In other words, the incorporation of Nd in each of the two growth steps is believed to be incomplete leading to a substantially lower final concentration for the dopant.

The Nd:YAG mini-rod was fused to the YAG fiber on the LHPG system. The fused assembly was supported horizontally, and the beam from the Ar ion laser was focused into the fiber end. A chromel-alumel thermocouple with 25 $\mu$m wires was used to monitor the temperature of the mini-rod. The unabsorbed portion of the laser power exiting the polished end of the mini-rod was monitored with a power meter. At an incident power level of a few milliwatts, the transmitted power was found to be 19%. When account is taken of the 8% per surface Fresnel loss for the air/YAG interface, comparison with transmissions measured for the separate pieces before fusion indicates that laser launching loss and scattering loss in the fused region together amounted to 21%. As the visually observed scattering from the fused region did not seem to be excessive, it is believed that the bulk of the above loss was associated with coupling of the laser beam into the fiber. The laser beam was deliberately focused to a relatively large spot in order to avoid damage to the polished fiber end.

Figure 4:
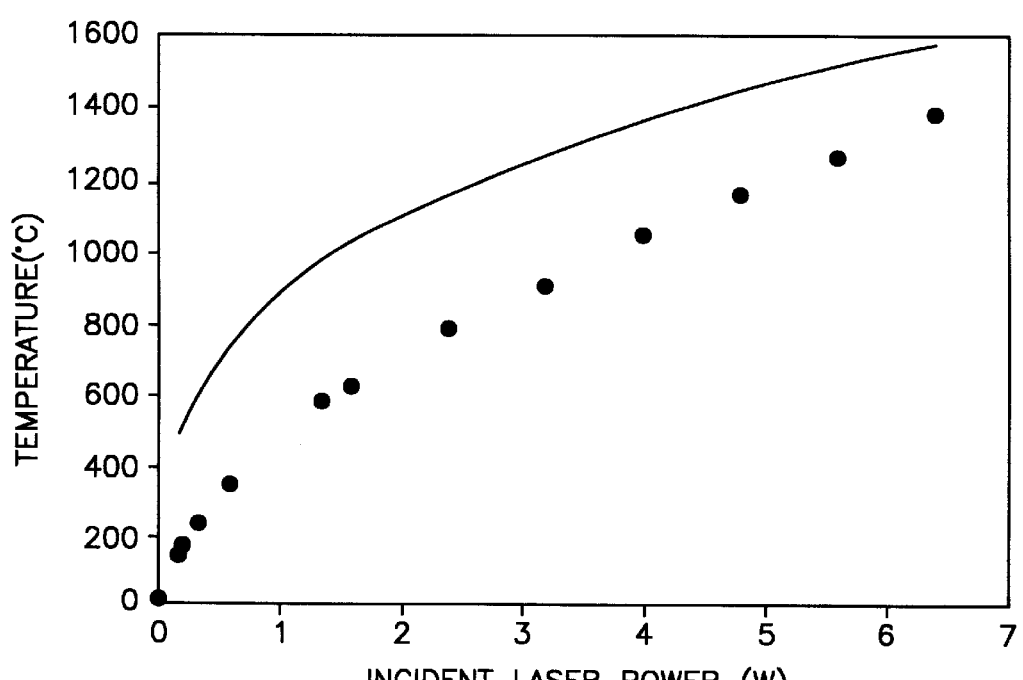
FIG. 4 is a graph of the results obtained in the working example of the present invention described below.

The fiberoptic heating element so made was tested using an argon ion laser capable of producing laser light at 514.5 nm wavelength. The results obtained are illustrated in FIG. 4. As can be seen from this figure, as the power of the incident laser beam was increased, the rate of temperature rise of the heat-generating tip was largest at first and then decreased at higher temperatures. The thermocouple was destroyed when the incident power exceeded the maximum value of 6.4 W shown in the figure. The fraction of incident power exiting the heat generating tip was measured to be essentially independent of the temperature throughout the entire range. Therefore, one can conclude from the known transmissions of 514.5 nm laser light through Nd-doped YAG that the absorbed power was approximately 45% of the incident power at all temperatures. On that basis, one can estimate the expected temperature of the heat-generating tip assuming black body radiation to be the only mechanism for thermal transport. This result is given by the curve in FIG. 4. It is seen that the agreement with experimental data is quite good at the high temperature end. Good agreement at the low temperature end should not be expected, as convective cooling and conduction loss at the attached fiber end become relatively more important in that region.

In order to test the ability of the device produced in this experiment to join microscopic components, an attempt was made to weld two 50 μm diameter gold wires. The wires were held in a fixture so that the ends just touched. The incident Ar ion laser power was increased to its maximum level of approximately 9 W, at which point the temperature of the mini-rod was believed to be about 1600° C. based on the data reported in FIG. 4. The point of contact of the gold wires was then pressed gently onto the side of the mini-rod. A small bead formed between the two wires, thus joining the two into a single piece. It was noted that there did not appear to be any wetting of the Nd:YAG heating element by the molten gold. This facilitated the joining process.

Other laser-powered fiberoptic heating elements having identical constructions as in the above working example were made, except that their heat-generating tip sections terminated in a point after some tapering, instead of a blunt polished end. These elements were also tested, and it was found that the heat-generating tip section of these elements invariably melted before the incident power reached 6 W. Since the melting temperature for YAG is 1,930° C., two conclusions can be drawn from these observations. First, strong temperature gradients can be created within the heat-generating tip sections by using a taper at the end. Second, the maximum temperature that can be achieved in this type of device is only limited by the melting temperature of the heat-generating tip section, and should easily exceed 2,000° C. when the appropriate material is used.

Many other variations and modifications of the invention will be apparent to those skilled in the art without departing from the spirit and scope of the invention. The above-described embodiments are therefore intended to be merely exemplary, and all such variations and modifications are intended to be included within the scope of the present invention.

We claim:

1. An fiberoptic heating element comprising a crystalline optic fiber and a crystalline heat-generating tip section fused thereto.

2. The heating element of claim 1, wherein said optic fiber is substantially transparent to laser light, and further wherein said heat-generating tip section is substantially opaque to laser light whereby laser light transmitted through said optic fiber is converted to thermal energy by said heat-generating tip section.

3. The heating element of claim 2, wherein said optic fiber and said heat-generating tip section are made from the same crystalline material, the crystalline material in said heat-generating tip section being doped with a dopant.

4. The heating element of claim 2, wherein said optic fiber and said heat-generating tip section are made from different crystalline materials.

5. The heating element of claim 4, wherein said optic fiber is made from a first crystalline material and said heat-generating tip section is made from a second crystalline material crystallographically compatible with said first crystalline material.

6. The heating element of claim 5, wherein the coefficients of thermal expansion of said first and second crystalline materials are sufficiently close so that said heat-generating tip section can be repeatedly heated and cooled between room temperature and an elevated temperature approaching the melting point of said heat-generating tip section without destruction of said heating element.

7. The heating element of claim 1, wherein the composition of said heat-generating tip section varies along its longitudinal direction whereby the generation of heat in said heat-generating tip section in response to irradiation with laser light varies along its longitudinal direction.

8. The heating element of claim 7, wherein the crystalline material forming said heat-generating tip section contains a dopant, the concentration of said dopant varying along the longitudinal direction of said heat-generating tip section.

9. The heating element of claim 1, wherein at least a portion of said heat-generating tip section is coated with a thin layer of metal.

10. The heating element of claim 1, further comprising a protective jacket on said optic fiber.

11. The heating element of claim 1, further comprising a secondary fiber attached to said optic fiber remote from said heat-generating tip section for transmitting laser light from a laser light source to said optic fiber.

12. The heating element of claim 1, wherein the diameter of said optic fiber is smallest at its point of attachment to said heat-generating tip section.

13. The heating element of claim 12, wherein said optic fiber includes a distal section attached to said heat-generating tip section and a proximal section remote from said heat-generating tip section, the diameter of said distal section being less than the diameter of said proximal section.

14. The heating element of claim 1, wherein said optic fiber is made from $Y_3Al_5O_{12}$ and further wherein said heat-generating tip element is made from $Y_3Al_5O_{12}$ doped with Nd.

15. The heating element of claim 1, wherein said heat-generating tip section is directly fusion bonded to said optic fiber.

16. The heating element of claim 1, further comprising a buffer crystal intermediate said heat-generating tip section and said optic fiber, said buffer crystal being fusion bonded to both said heat-generating tip section and said optic fiber.

17. The heating element of claim 1, wherein said tip section tapers to a point.

18. The fiberoptic heating element of claim 1, wherein said crystalline heating element is fused to said crystalline optic fiber without adhesive.

19. The fiberoptic heating element of claim 18, wherein the crystalline heating element is attached to the optic fiber without adhesive.

20. The fiberoptic heating element of claim 1, wherein said crystalline heating element is fused to said crystalline optic fiber by heating.

21. The fiberoptic heating element of claim 1, wherein said crystalline heating element is fused to said crystalline optic fiber by growing said crystalline heating element on said optic fiber.

22. The fiberoptic heating element of claim 1, wherein the crystalline optic fiber has a distal end face, the distal end face of the optic fiber being fused to the crystalline heat-generating tip section.

23. A heating assembly comprising
(a) a laser capable of producing laser light at a predetermined wavelength and
(b) a fiberoptic heating element for converting said laser light to heat, said heating element comprising an optic fiber for receiving laser light produced by said laser, said optic fiber being substantially transparent to said laser light, and a crystalline heat-generating tip section fused to said optic fiber, said heat-generating tip section being substantially opaque to laser light whereby laser light transmitted through said optic fiber is converted to thermal energy by said heat-generating tip section.

24. The heating assembly of claim 23, wherein said optic fiber is made from a first crystalline material and said heat-generating tip section is made from a second crystalline material crystallographically compatible with said first crystalline material, and further wherein the coefficients of thermal expansion of said first and second crystalline materials are sufficiently close so that said heat-generating tip section can be repeatedly heated and cooled between room temperature and an elevated temperature approaching the melting point of said heat-generating tip section without destruction of said heating element.

25. The heating element of claim 23, wherein said optic fiber and said heat-generating tip section are made from the same crystalline material, the crystalline material in said heat-generating tip section being doped with a dopant.

26. A fiberoptic heating element comprising a crystalline optic fiber made from a first crystalline material and a crystalline heat-generating tip section made from a second crystalline material, the crystalline optic fiber and the crystalline heat-generating tip section being joined to one another at a junction, the first crystalline material and the second crystalline material being fused to one another at the junction.

27. The fiberoptic heating element of claims 26, wherein the first and second crystalline materials are compatible with one another.

28. The fiberoptic heating element of claim 26, wherein the crystalline optic fiber has a distal end face, the distal end face of the optic fiber being fused to the crystalline heat-generating tip section at the junction.

29. The fiberoptic heating element of claim 26, wherein the crystal structure of the crystalline heat-generating tip section and the crystal structure of the crystalline optic fiber match.

30. The fiberoptic heating element of claim 26, wherein the crystal structure of the crystalline heat-generating tip section registers with the crystal structure of the crystalline optic fiber.

31. A fiberoptic heating element comprising a crystalline optic fiber made from a first crystalline material and a crystalline heat-generating tip section made from a second crystalline material, the crystalline optic fiber and the crystalline heat-generating tip section being fused to one another at a junction, the material fusing the crystalline optic fiber and the crystalline heat-generating tip section together at their junction consisting essentially of the first crystalline material and the second crystalline material.

32. The fiberoptic heating element of claim 31, wherein the material fusing the crystalline optic fiber and the crystalline heat-generating tip section together at their junction consists of the first crystalline material and the second crystalline material.

33. The fiberoptic heating element of claim 31, wherein the crystalline optic fiber has a distal end face, the distal end face of the optic fiber being fused to the crystalline heat-generating tip section at the junction.

\* \* \* \* \*